United States Patent [19]

Gard, Jr. et al.

[11] Patent Number: 5,147,640

[45] Date of Patent: Sep. 15, 1992

[54] **STRAINS OF *BACILLUS THURINGIENSIS* INSECTICIDAL COMPOSITIONS CONTAINING THE SAME**

[75] Inventors: Ivan E. Gard, Jr., Holland, Pa.; Jose M. Gonzalez, Jr., West Trenton, N.J.; Dennis R. Ciarlante, Newtown, Pa.

[73] Assignee: Ecogen Inc., Langhorne, Pa.

[21] Appl. No.: 268,307

[22] Filed: Nov. 7, 1988

[51] Int. Cl.$^5$ .................. A01N 63/00; C12N 1/20
[52] U.S. Cl. .................. 424/93 A; 514/2; 424/405; 424/93 L; 435/252.31
[58] Field of Search .............. 514/2; 424/405, 93; 435/253, 252.31

[56] References Cited

U.S. PATENT DOCUMENTS

| | | | |
|---|---|---|---|
| 4,081,267 | 3/1978 | Hashimoto et al. | 71/93 |
| 4,696,938 | 9/1987 | Le | 514/343 |
| 4,713,241 | 12/1987 | Wakisaka et al. | 424/93 |
| 4,857,510 | 8/1989 | Knauf et al. | 514/30 |
| 4,902,507 | 2/1990 | Morris et al. | 424/93 |
| 4,935,353 | 6/1990 | Burger et al. | 435/69.1 |

FOREIGN PATENT DOCUMENTS 8808877 11/1988 PCT Int'l Appl. .

OTHER PUBLICATIONS

Hughes, H. A., 1976. *Fundamental of Machine-Operation: Pop Chemicals*, John Deere Service Publication, Moline, Ill.

Knowles et al. 1986, J. Cell Sci. 84:221–236.

Jarrett, "Potency factors in the delta-endotoxin of *Bacillus thuringiensis* var. aizawai . . . ", *J. App. Bact.* (1985) 58:437–448.

McGaughey et al., J. Econ. Entomol 80(6): 1122–1126 (1987); Dec. 1987.

Mohamad et al., Insect. Sci. Appl. 9(1): 109–112 (1988).

European Patent Publication No. 0178 151 published Apr. 16, 1986 of Agricultural Genetics Co. Ltd.

Knowles et al., "Differential specifity of two insecticidal toxins . . . ", *Mol. Microbiol.* (1988) 2:153–157.

Sanchis et al., "Multiplicity of beta-endotoxin genes . . . ", *Mol. Microbiol.* (1988) 2:393–404.

Sekar, "Location of Crystal Toxin Gene . . . ", *Curr. Microbiol.* (1987) 14:301–304.

Gonzalez, Jr. et al., "Transfer of *Bacillus thuringiensis* plasmids . . . ", *Proc. Natl. Acad. Sci. USA* (1982) 79:6951–6955.

*Primary Examiner*—Margaret Moskowitz
*Assistant Examiner*—Keith C. Furman
*Attorney, Agent, or Firm*—Christopher Egolf

[57] ABSTRACT

The present invention provides novel strains of *Bacillus thuringiensis* containing genes that code for P1 endotoxin proteins. The invention also provides methods and compositions for controlling insects or protecting plants from insect attack with a novel strain of *Bacillus thuringiensis*.

5 Claims, No Drawings

STRAINS OF *BACILLUS THURINGIENSIS* INSECTICIDAL COMPOSITIONS CONTAINING THE SAME

BACKGROUND OF THE INVENTION

Although the art is replete with references relating to *Bacillus thuringiensis* (B.t.), its manufacture and use for controlling a variety of insect species, nevertheless, it has been found that certain species of insects, such as *Plutella xylostella*, are not effectively controlled by commercially available strains of *Bacillus thuringiensis* or many conventional insecticides such as the carbamates, phosphates and pyrethroids.

It is therefore an object of the present invention to provide novel strains of *Bacillus thuringiensis* that retain the desirable attributes of biopesticides while providing greatly enhanced control of insect populations that have developed resistance to conventional insecticides and that are not effectively controlled by commercially commercialavailable strains of *Bacillus thuringiensis*.

It is also an object of this invention to provide novel solid and liquid B.t. compositions that are highly effective for controlling *Plutella xylostella* and/or for protecting plants from attack thereby, said compositions containing an insecticidally effective amount of a novel *Bacillus thuringiensis* strain.

DESCRIPTION OF THE INVENTION

The present invention relates to novel strains of *Bacillus thuringiensis* containing a 110 megadalton plasmid which codes for P1 endotoxin proteins and a 46 or a 65 megadalton plasmid that codes for P1 endotoxin proteins. The invention further relates to a method for controlling insects, particularly lepidopteran insects and especially *Plutella xylostella* with an insecticidally effective amount of a B.t. composition in which the B.t. strain has a 110 megadalton plasmid and a 46 or 65 megadalton plasmid. The invention also relates to a method for protecting plants from the ravages of feeding insects by applying to the foliage of said plants an insecticidally effective amount of a strain of *Bacillus thuringiensis* having a 110 megadalton plasmid and either a 46 or 65 megadalton plasmid.

*Bacillus thruingiensis*, frequently referred to as B.t., is a spore-forming microorganism that produces endotoxins during its sporulation cycle. The endotoxins are proteins which are generally deposited as parasporal crystals and are the primary factor determining the effectiveness of a specific B.t. strain as an insecticidal agent. It has been found that, during sporulation, different strains of B.t. frequently produce different endotoxins and different quantities thereof. For example, it has been found that certain strains of B.t. produce very limited quantities of endotoxins and parasporal crystals, whereas, other B.t. strains can produce crystals equivalent to about 15% to 40% of the dry weight of the B.t. cells. Thus, it is evident that the insecticidal activity of a new strain of B.t. can only be established by proper evaluation.

Surprisingly, we have now discovered that the effective control of certain insects such as *Plutella xylostella* with B.t. is largely attributable to the combined presence in the B.t. composition, of the 110 megadalton plasmid which carries the genetic information (gene(s)) encoding for P1 endotoxin proteins and either the 46 or 65 megadalton plasmid which carries the genetic information (gene(s)) encoding for P1 endotoxin proteins.

Moreover, we have found that B.t. strains, particularly var. aizawai (Serovar H7), with the following plasmid profiles in megadaltons (Md) are especially effective for controlling *Plutella xylostella* and/of deterring said pest from feeding on the foliage of plants, when said plants are sprayed with a liquid composition containing one of said B.t. strains.

The plasmid profiles of B.t. strain HD122-1 var. aizawai and variants in megadaltons (Md) which are preferred for use in this invention as insect control agents or plant protection agents, are as follows:

HD122-1—designated "wild type" ~120, ~110+, 78, 50, 46+, 43, 33, 31, 30, 6.0 open circular (o.c.), 8.0, 7.9, 5.4, 4.7, 3.5, linear D.N.A. element (L.D.E.); where + designates a plasmid encoding insecticidal toxin protein;

HD-122A—~120, ~110+, 78, 50, 46+, 43, 33, 31, 8.0, 7.9, 6.0 (o.c.), 5.4, 4.7, 3.5, L.D.E.;

HD-122B—~120, ~110+, 78, 65+, 50, 43, 33, 30, 6.0 (o.c.), 8.0, 7.9, 5.4, 4.7, 3.5, L.D.E.; and HD-122C—~120, ~110+, 78, 50, 46+, 43, 33, 31, 30, 6.0 (o.c.), 8.0, 5.4, 4.7, 3.5, L.D.E.

The 110 Md plasmid of Bt strain HD122-1 var. aizawai and its variants (HD-122A, HD-122B, HD-122C) carry the genetic information to encode one or more endotoxin proteins approximately 130–145 kilodaltons (kD) in size. Likewise, the 46 and 65 Md plasmids carry the genetic information to encode an endotoxin protein of approximately 130–140 kD in size. These endotoxin proteins, produced upon sporulation, form bipyramidal crystalline inclusions that are insecticidal to larvae of *Plutella xylostella*.

In addition to the above, the loss of a 46+ or 65+ plasmid from any of the above compositions results in a significant loss of insecticidal activity and plant protection activity of the B.t. composition having the reduced plasmid array.

As indicated, the B.t. strains of this invention are highly effective for the control of *Plutella xylostella* and find special utility for the control thereof. However, the B.t. strains of this invention are likewise useful for controlling a variety of other insects such as *Spodoptera exiqua*, the beet armyworm; *Trichoplusia ni*, the cabbage looper; *Heliothis zea*, the bollworm, corn earworm or tomato fruitworm; *Heliothis virescens*, the tobacco budworm; the armyworms *spodoptera littoralis*, *Spodoptera frugiperda*, and *Spodoptera eridania* and the imported cabbageworm, *Pieris rapae*.

Control of said insects and/or protection of plants upon which such insects feed is generally achieved by applying to the foliage of plants, a liquid spray containing an insecticidally effective amount of an endotoxin protein produced by a B.t. strain having the 110+ megadalton plasmid and either a 46+ or 65+ megadalton plasmid. Ingestion of the treated plants by feeding insects permits the B.t. endotoxin to enter the mid-gut of the insect where the alkaline pH and proteolytic enzymes in the insects gut dissolve the parasporal crystals of the B.t. endotoxin composition activating the toxin produced by the 110+ and 46+ or 65+ megadalton plasmids of the applied spray composition.

The thus activated toxin disrupts the mid-gut cells causing the insect to stop feeding and die.

Liquid compositions containing about 10 to 10000 ppm and preferably about 20 to 500 ppm of the endotoxin protein produced by a B.t. strain containing a 110+ megadalton plasmid and a 46+ or 65+ megadalton plasmid are effective for achieving the insect control and plant protection desired.

We have found that the B.t. strains of this invention are highly effective for controlling *Plutella xylostella* as well as other lepidopteran pests and are useful for protecting plants from attack by such insect pests when applied to said insects' feed or feeding grounds at application rates of about 10 grams to 10,000 grams of toxin protein per hectare and preferably about 20 grams to 500 grams of toxin protein per hectare.

The B.t. strains of the present invention are advantageously prepared as fermentation broth concentrates which consist of dewatered fermentation broth containing about 15%–40% w/v of fermentation insolubles, with no additional chemicals or additives beyond those present in the fermentation media. The concentrate generally contains, but is not limited to, about 1% to 20% w/v of B.t. endotoxin protein. The fermentation broth concentrate can be formulated directly into an insecticide liquid spray or it may be spray dried and the spray dried material formulated as a wettable powder, an oil flowable concentrate, aqueous flowable formulation, water dispersible granule, microencapsulated formulation and/or other formulations. These formulations can be prepared by admixing the spray dried B.t. powder with formulation ingredients such as surfactants, viscosifiers, inert solid or liquid diluents and the like.

Wettable powder formulations that can be prepared with spray dried B.t. may contain from 1% to 20% by weight of B.t. crystals; 14% to 20% by weight of fermentation insolubles; 40% to 60% by weight of a diluent such as attapulgite, kaolinite, montmorillonite, diatomaceous earth, talc or the like; 5% to 10% by weight of a wetting agent; 2% to 8% by weight of a nonionic emulsifying agent and about 1% to 3% by weight of a conditioning agent.

Typical wettable powder formulations frequently contain about 15% to 20% of B.t. crystals; about 14% to 20% of fermentation insolubles; 45% to 55% attapulgite or kaolin; 2% synthetic silicate conditioning agent; 2.5% to 5% of an emulsifying agent such as sorbitan monooleate; 0% to 2.5% of a wetting agent such as octylphenoxy polyethoxy ethanol and 0% to about 0.5% of polyvinylpyrrolidone.

Oil flowable formulations of B.t. strains used in the methods of the present invention generally contain about 10% to 15% by weight of B.t. crystals produced by B.t. cells containing the 110+ megadalton plasmid and either the 46+ or 65+ megadalton plasmid; about 10% to 15% of fermentation insolubles; about 2% to 3% of a hydrogenated castor oil; 0% to 1.0% lactose; 5% to 10% of an emulsifying agent and 50% to 65% by weight of an oil, such as a paraffinic hydrocarbon or mineral oil.

While many highly active insecticidal B.t. strains are produced by transconjugation, other highly active B.t. strains may require the initial elimination of one or more plasmids from a multiple toxin plasmid B.t. strain before the transfer of a selected plasmid thereto. Loss of a plasmid is referred to as curing and it has been found that curing can lead to a predominance of certain toxin proteins. Curing of a B.t. strain may thus be employed as a means for increasing not only the toxicity of the B.t. strain, but also the selectivity or specificity of the B.t. strain against a given insect, insect species or insect order.

The present invention is further illustrated by the examples set forth below.

EXAMPLE 1

Fermentation Process for Preparation of *Bacillus Thuringiensis* (B.t.) Strain HD-122A Var. Aizawai (EG2175) on Medium C-2M The fermentation inoculum consists of an aseptic spore suspension of strain HD-122A var. aizawai also known as EG2175. This is prepared by aseptically inoculating a loop from a single isolated colony of this strain on nutrient salts agar (NSA) (Table I) into 500 ml. of C-2 medium in a baffled, 2 liter Erlenmeyer flask. This flask is shaken for 48 hours (300 RPM) at 30° C., whereupon a fully sporulated culture is formed. This is stable for several weeks and is preferably refrigerated. An aliquot of seed is then aseptically removed prior to use and 100 microliters plated as a confluent surface lawn on NSA (Table I) to verify purity (incubate at 30° C.). A second streak plate containing a confluent area and isolated colonies is made on NSA agar and DNA extracted from both colonies and the confluent area run on an Eckhardt agarose gel according to the procedure of Gonzalez (Ref. 1) against a standard of known strain EG2175. The plasmid profiles are compared to verify that the inoculum is pure EG2175 and has not become genetically altered.

The fermenter is then filled with medium C2M (Table II) and sterilized. A 45 minute sterilization at 121° C. is recommended. The phosphate and glucose are separately sterilized and added to the cooled balance as shots. This medium is adjusted to pH 7.2 prior to sterilization with 5N NaOH or $H_3PO_4$. A sample of the sterile complete medium is drawn and 500 microliters plated (surface spread) on NSA to verify sterility.

The medium is inoculated by aseptic transfer of 1 vol. % spore suspension, although 0.1–10 vol. % can be used. A sample is taken immediately after inoculation and 100 µl plated on NSA to verify purity. The fermenter is kept at 30° C. and agitator RPM and air rate adjusted to maintain dissolved oxygen (DO) at a minimum of 20% saturation. The pH is controlled at 7.0 (range 6.8-7.2) by aseptic addition of 5N $H_3PO_4$ or NaOH, as required. Variables to be recorded or logged include pH, temperature, RPM, air rate, DO, and head pressure (P). The spores germinate within 2–4 hours and vegetative growth begins. Aseptic samples are taken, preferably every two hours, and (a) a wet mount examined in the phase contrast microscope, oil immersion, 1000x, and the appearance recorded; and (b) Glucose concentration measured by YSI or similar device. Foaming should not be significant, but Mazu DF204 antifoam (Mazer Chemical, Gurnee Ill.) should be available for aseptic addition as required.

The cells in the fermenter begin to sporulate at 12–16 hours, and are generally fully sporulated and lysed at 24–36 hours. Sporulation is indicated by the appearance of phase bright, oval polar spores and also somewhat phase bright protein crystals within the cell confines or sporangium. Lysis is indicated by release of free spores and crystals from the sporangium.

The culture is harvested by use either of a hollow fibre, cross flow membrane system, e.g. Romicon Pilot-Pro10 or a disk-stack centrifuge, e.g. Alfa-Laval AX213. In the Romicon, using 106 mil PM500 fibres, recirculation rate is held at a value which maintains inlet and outlet pressures at 10 and 40 PSI, respectively.

Harvesting is continued until concentrate volume is reduced to 5-15% of original broth volume. Preferably, concentrate is then washed twice with equal volumes of tap water by repulping and reconcentrating. If the centrifuge is used, flow rate and discharge frequency are adjusted so that few protein crystals are visible by phase contrast microscopy in the supernatant.

TABLE I

| Nutrient Salts Agar (NSA) | |
|---|---|
| | g/L |
| Nutrient Broth (Difco) | 8 |
| Agar | 15 |
| $MgCl_2.6H_2O$ | 0.2 |
| $CaCl_2.2H_2O$ | 0.103 |
| $MnCl_2.4H_2O$ | 0.01 |

Note: The salts are required to obtain good sporulation of B.t. which will not occur on plain nutrient agar (NA).

TABLE II

| | C-2M Medium gm/liter | | C-2 Medium gm/liter |
|---|---|---|---|
| Glucose | 10 (1) | Glucose | 10 (1) |
| Marcor Casein B | 2 | Bacto Peptone | 2 |
| Amberex 1003 Yeast Est. | 2 | Difco Yeast Extract | 2 |
| NZ Amine A | 5 | NZ Amine A | 5 |
| Phosphates (2) | | | |
| $KH_2PO_4$ | 0.311 | | 3.11' |
| $K_2HPO_4$ | 0.466 | | 4.66 |
| Salts | | Salts | |
| $MgSO_4.7H_2O$ | 0.3 | $MgSO_4.7H_2O$ | 0.3 |
| $CaCl_2.2H_2O$ | 0.1 | $CaCl_2.2H_2O$ | 0.1 |
| $MnCl_2.4H_2O$ | 0.058 | $MnCl_2.4H_2O$ | 0.058 |
| $(NH_4)_2SO_4$ | 2.0 | $(NH_4)_2SO_4$ | 2.0 |
| $ZnSO_4.7H_2O$ | 0.005 | $ZnSO_4.7H_2O$ | 0.005 |
| $CuSO_4.5H_2O$ | 0.005 | $CuSO_4.5H_2O$ | 0.005 |
| $FeSO_4.7H_2O$ | 0.0005 | $FeSO_4.7H_2O$ | 0.0005 |
| Antifoam, Mazu 64P | 0.25 ml | | |
| (add before sterilization) | | | |
| pH 7.2; adjust as required with 5 N NaOH or $H_2SO_4$. | | | |

(1) As anhydrous, use 100% of this if monohydrate (e.g. cerelose) is used. Separately sterilized as 50-70% solution and aseptically added to balance of sterile, cooled medium.
(2) Prepared as a concentrated solution, separately sterilized and aseptically added to balance of sterile, cooled medium in fermenter.
Ref. 1: Gonzales, J. M., Dulmage, H. T., Carlton, B. C., Plasmid, v. 5, P. 351-365 (1981).

As previously indicated HD122-1 (EG2179) is considered to be a wild type or parental strain of B.t., from which the other variants (HD-122A, HD-b 122B, HD-122C) originate through plasmid changes. All four strains are isolated as biologically pure cultures on nutrient salts agar and characterized with respect to plasmid array.

HD122-1 (EG2179) has the following plasmid array: 3.5, 4.7, 5.4, 7.9, 8.0, ~6.0 (open circular), L.D.E., 30, 31, 33, 43, 46+, 50, 78, 110+, ~120 (plasmid sizes in megadaltons).

The three variant strains isolated differ as follows from HD122-1.

HD-122A (EG2175) lacks the 30 MD plasmid.
HD-122B (EG2176) lacks the 31 Md plasmid; the 46+-Md is replaced by a 65+ Md toxin plasmid.
HD-122C (EG2177) lacks the 7.9-Md plasmid.

The plasmid profiles of these HD122 variants in megadaltons (Md) are preferred for use in this invention as insect control agents or plant protection agents, and can be illustrated as follows:
HD-122A—~120, ~110+, 78, 50, 46+, 43, 33, 31, 8.0, 7.9, 6.0 (o.c.), 5.4, 4.7, 3.5, L.D.E.;
HD-122B—~120, ~110+, 78, 65+, 50, 43, 33, 30, 6.0 (o.c.), 8.0, 7.9, 5.4, 4.7, 3.5, L.D.E., and
HD-122C—~120, ~110+, 78, 50, 46+, 43, 33, 31, 30, 6.0 (o.c.), 8.0, 5.4, 4.7, 3.5, L.D.E.

EXAMPLE 2

Isolation of HD263-1 (EG2035) var. kurstaki HD-263-1

The B.t. var. kurstaki strain HD-263 is obtained from the U.S.D.A. culture collection.

A single colony representative of the culture is isolated and chosen as the wild-type, or parental strain. This colony, HD263-1 (EG2035), has the following plasmid array: 1.4, 4.9, 5.0, 5.2, 5.4, 7.5, 43, 44+, 60+, 110+, and 130 (sizes in megadaltons, Md).

HD-263 is available from the NRRL culture collection, U.S.D.A., Peoria, Ill., as NRRL-HD-263.

EXAMPLE 3

Isolation of HD263-4 (EG2038) var. kurstaki

The HD263 parental strain, HD263-1 (EG2035), contains three toxin plasmids of sizes 110 Md, 60 Md, and 44 Md. HD263-1 is grown with shaking in Difco nutrient broth at an elevated temperature (42° C.) overnight, then single colonies are isolated from the overnight culture. A colony that has lost the 44 Md toxin plasmid is discovered by random screening of single colonies on agarose gels, to detect the absence of the 4 4Md plasmid, and named HD263-4.

EXAMPLE 4

Isolation of HD263-4-5A (EG2101), var. kurstaki

The B.t. strain HD-122A (EG2175) was used as a donor by growing it together with recipient strain HD73-26 by inoculating spores of both strains into M27 broth (composition described in Section 6.1 below) and allowing the strains to grow together for 8 hours at 30° C., with gentle shaking. Afterwards, colonies of the recipient strain are selected by using streptomycin containing plates (HD73-26 is resistant to streptomycin) and Cry+ (crystal producing) colonies are then identified by phase contrast microscopy. In this manner, the transconjugant HD73-26-23 (EG2255) is created, and has acquired the 46+ and 5.4 Md plasmids from HD-122A. HD73-26-23 is then used as a donor by inoculating its spores and those of the recipient strain HD263-4 (EG2038) together into M27 broth and growing them together at 30° C. for 8 hours with gentle shaking. The transconjugant HD263-4-5A (EG2101), which has acquired the 46+ Md P1 toxin plasmid from HD73-26-23, is isolated by random screening of recipient-type (P1-P2+) colonies on agarose gels.

EXAMPLE 5

Isolation of HD279 (EG2154) var. kurstaki

The B.t. var. kurstaki strain HD-279 is obtained from the U.S.D.A. culture collection.

A single colony representative of the culture is isolated and chosen as the wild-type, or parental strain. This colony, HD279-1 (EG2154), has the following plasmid array: 1.4, 4.9, 5.0, 5.2, 5.4, 7.2, 7.5, L.D.E., 43, 44+, 48, 60+, 110+, and 130 (sizes in megadaltons, Md).

HD-279 is available from the NRRL culture collection, U.S.D.A., Peoria, Ill., as NRRL-HD-279.

EXAMPLE 6

Isolation of HD279-72 var. kurstaki

The HD-279 parental strain, HD279-1 (EG2154), contains three toxin plasmids of sizes 110 Md, 60 Md, and 44 Md. HD279-1 is grown on Luria Agar (1% Peptone, 0.5% Yeast Extract, 0.5% NaCl, 1.2% agar) at an elevated temperature (43° C.) for several days, then colonies derived from single cells are isolated from the overgrown colony. A colony that has lost the 60 Md toxin plasmid is discovered by random screening of single colonies on agarose gels and is named HD279-72 (EG2157).

EXAMPLE 7

Evaluation of Test *Bacillus Thuringiensis* Composition as insect Control Agents Against *Plutella Xylostella*

In the following evaluations spray dried B.t. powders are dispersed in 50/50 water/acetone mixtures in sufficient amounts to provide from 30 to 1000 ppm of the B.t. strain to be evaluated. To ensure that the technical material is completely suspended, the mixture is then placed in a sonifier for about 5 minutes.

Leaves of head cabbage or chinese cabbage are then dipped or sprayed with test solutions and the wet leaves then permitted to dry. Treated leaves are placed in petri dishes (150×20 mm) lined with moist filter paper and inoculated with 10 third instar Diamondback Moth—*Plutella xylostella* larvae. Mortality is recorded 24, 72 and 120 hours after the tests are initiated and results are recorded. The feeding rate of the insects is also determined at 72 hours after the test is initiated.

The B.t. strains used in this evaluation are identified below by plasmid array reported in megadaltons.
HD263-1 (EG2035):
  Prototype strain, var. kurstaki, from England.
  Plasmids: 130, 110, 60, 44, 43, 7.5, 5.4, 5.2, 5.0, 4.9, 1.4 Md.
  Toxin plasmids: 110 (P1, P2), 60 (P1), 44 (P1)
HD263-4 (EG2038):
  Strain HD263-1 cured of the 44 Md toxin plasmid.
  Toxin plasmids: 110 (P1, P2), 60 (P1)
HD263-4-5A (EG2101):
  Transconjugant using HD263-4 as recipient that has acquired the 46 Md (P1) toxin plasmid of HD-122A.
  Toxin plasmids: 110 (P1, P2), 60 (P1) and 46 (P1)

Dipel is *Bacillus thuringiensis*, a product of Abbott Laboratories, used for comparison.

An untreated control is also used in these evaluations.

Data obtained in the plant spray test are reported below in Table III and show that the 46 Md plasmid from HD-122A enhances the activity of strain HD263-4. It should be noted that the 110 Md plasmid of HD263-1, HD263-4 and HD263-4-5A encodes different insecticidal proteins than does the 110 Md plasmid of HD122-1, HD122A, HD122B and HD122C.

TABLE III

Effect of B.t. compounds applied as plant spray against resistant *Plutella xylostella*

| Treatment | Conc. (ppm) Formulation | % Mortality 24 H | 72 H | 120 H | Feeding rate (72 Hours) |
|---|---|---|---|---|---|
| HD263-1 | 50 | 13.0 | 100.0 | 100.0 | Moderate |
|  | 100 | 50.0 | 100.0 | 100.0 | Moderate |
|  | 200 | 88.0 | 100.0 | 100.0 | Light |
|  | 400 | 75.0 | 100.0 | 100.0 | Slight |
| HD263-4 | 100 | 0.0 | 63.0 | 63.0 | Heavy |
|  | 200 | 13.0 | 43.0 | 43.0 | Heavy |
|  | 400 | 22.0 | 100.0 | 100.0 | Light |
|  | 600 | 60.0 | 100.0 | 100.0 | Light |
| HD263-4-5A | 50 | 25.0 | 100.0 | 100.0 | Moderate |
|  | 100 | 25.0 | 100.0 | 100.0 | Moderate |
|  | 200 | 50.0 | 100.0 | 100.0 | Light |
|  | 400 | 75.0 | 100.0 | 100.0 | Slight |
| Dipel | 300 | 40.0 | 100.0 | 100.0 | Light |
| Control | — | 0.0 | 0.0 | 10.0 | Heavy |

Damage Rating Systems

0=no damage
1=Slight or about 1 to 5% of leaf area is consumed
3=Light or about 10 to 20% of leaf area is consumed
5=Moderate or about 30 to 40% of leaf area is consumed
7=Heavy or about 50 to 60% of leaf area is consumed
9=Severe or about 70% and above of leaf area is consumed Ratings of 2, 4, 6 or 8 simply mean that the damage observed falls between the above indicated ratings and ratings shown with a decimal are average ratings from 6 plants.

EXAMPLE 8

Evaluation of B.t. Test Compositions for Protection of Cabbage Plants Against *Plutella Xylostella*

In this test spray dried B.t. samples are prepared as wettable powders comprising about 10% by weight B.t. crystals; 22.5% B.t. fermentation solids; 52.75% kaolinite (clay) diluent; 8% wetting agent; 5% nonionic emulsifying agent and 2% of a synthetic conditioning agent.

Cabbage plants are grown in a screen house which simulates field conditions but limits insect infestation to the insect introduced into the screen house. In this test, Diamondback Moth larvae (*Plutella xylostella*) were introduced permitting infestation of the cabbage plants. The plants are sprayed at 4 day intervals with the test compositions and the number of 1–2 instar and 3–4 instar larvae per plant counted and feeding damage evaluated on day 1 and on days 4 and 7 after treatment is initiated.

The damage rating scale used in this test is as follows:

Damage Rating Systems

0=no damage
1=Slight or about 1 to 5% of leaf area is consumed
3=Light or about 10 to 20% of leaf area is consumed 5 = Moderate or about 30 to 40% of leaf area is consumed
7 = Heavy or about 50 to 60% of leaf area is consumed
9 = Severe or about 70% and above of leaf area is consumed Ratings of 2, 4, 6 or 8 simply mean that the damage observed falls between the above indicated ratings and ratings shown with a decimal are average ratings from 6 plants.

Data obtained are reported in Table IV below.

TABLE IV

Evaluation of B.t. test compositions for controlling *Plutella xylostella* and inhibiting damage to cabbage plants by application thereto of the B.t. test compositions

| Treatment | % ai[1] (wt/wt) | gm ai/ha | Larvae/plant | | | | | | Damage Rating day 7 |
|---|---|---|---|---|---|---|---|---|---|
| | | | day 1 | | day 4 | | day 7 | | |
| | | | 1-2 Instar | 3-4 Instar | 1-2 Instar | 3-4 Instar | 1-2 Instar | 3-4 Instar | |
| HD279 | 6.8% | 30 | 8.8 | 0.9 | 6.6 | 0.9 | 6.4 | 2.3 | 3.9 |
| | | 60 | 5.5 | 0.5 | 3.2 | 0.5 | 3.3 | 1.0 | 3.6 |
| HD279-72 | 6.15% | 30 | 8.5 | 1.3 | 4.9 | 0.8 | 4.0 | 1.4 | 2.8 |
| | | 60 | 8.9 | 1.9 | 4.8 | 1.8 | 4.3 | 1.6 | 3.7 |
| HD122A | 12% | 15 | 7.7 | 0.2 | 4.0 | 0.3 | 4.2 | 0.8 | 2.3 |
| | | 30 | 8.1 | 0.4 | 5.3 | 0.2 | 4.5 | 0.5 | 2.6 |
| | | 60 | 2.0 | 0.2 | 0.5 | 0.0 | 0.5 | 0.6 | 1.0 |
| Dipel | 12% | 60 | 11.8 | 2.3 | 5.7 | 1.4 | 4.6 | 1.9 | 4.9 |
| | | 120 | 11.6 | 2.8 | 7.7 | 1.1 | 6.6 | 1.8 | 4.9 |
| | | 240 | 10.6 | 1.1 | 7.8 | 1.1 | 7.5 | 1.8 | 4.3 |
| Untreated | | — | 9.8 | 5.8 | 9.7 | 4.4 | 6.3 | 3.8 | 7.4 |

[1] ai = active ingredient or toxin protein

From the above data it can be seen that 15 grams of toxin protein per hectare of HD-122A having a 110 Md plasmid and a 46 Md plasmid gives better insect control and better plant protection against *Plutella xylostella* attack than 60 grams per hectare of B.t. strains that do not contain the 110 Md plasmid and the 46 or 65 Md plasmid of HD-122A.

EXAMPLE 9

Evaluation of B.t. Strain HD-122A (EG2175) for the Control of *Plutella Xylostella*

In this evaluation B.t. strain HD-122A (EG2175) var. aizawai, having the following plasmid array; Plasmids: 120, 110, 78, 50, 46, 43, 33, 31, 6.0 (O.C.) 8.0, 5.4, 3.5 Md and L.D.E. Toxin Plasmids: 110 (P1), 46 (P1); is prepared as a spray dried B.t. powder and formulated as a wettable powder for application in the form of a liquid spray. The formulated compositions comprises 10% by weight of B.t. crystals; 22.25% B.t., fermentation solids; 52.75% of a kaolinite (clay) diluent; 8% of a wetting agent; 5% of a nonionic emulsifying agent and 2% of a synthetic silicate conditioning agent.

Other diluents, wetting agents and dispersing agents that can be used in preparation of B.t. wettable powders include: attapulgite and bentonite diluents; tetramethyl dicynediol, sodium alkyl sulfonate and nonyl phenol ethoxylate wetting agents and sodium naphthalene sulfonic acid dispersing agents.

The damage rating system used in these evaluations is as follows:

Damage Rating Systems

0 = no damage
1 = Slight or about 1 to 5% of leaf area is consumed
3 = Light or about 10 to 20% of leaf area is consumed
5 = Moderate or about 30 to 40% of leaf area is consumed
7'Heavy or about 50 to 60% of leaf area is consumed
9 = Severe or about 70% and above of leaf area is consumed Ratings of 2, 4, 6 or 8 simply mean that the damage observed falls between the above indicated ratings and ratings shown with a decimal are average ratings from 6 plants.

In these tests, cabbage plants growing in field plots known to be heavily infested with resistant *Plutella xylostella*, are sprayed with aqueous dispersions of test compounds. Spray applications are applied to cabbage plants in sufficient amount to provide form about 15 to 490 grams per hectare of the active compound being evaluated. Three and six days after the fourth spray application, 6 plants per plot are examined for larvae numbers and plant damage.

These ratings are reported in Table V below.

TABLE V

Comparative effect of HD-122A and Dipel applied at 4 days interval against resistant *Plutella xylostella*

| Treatment | gm ai/ha | Larvae/Plant[1] | | | | Damage ratings[2] | |
|---|---|---|---|---|---|---|---|
| | | 3 days post | | 6 days post | | 3rd spray | 4th spray |
| | | 1-2 | 3-4 | 1-2 | 3-4 | | |
| HD-122A 12% | 15 | 6.7 | 3.7 | 9.3 | 3.0 | 3.8 | 4.9 |
| | 30 | 5.6 | 0.7 | 7.4 | 1.1 | 2.9 | 3.8 |
| | 60 | 3.4 | 0.3 | 4.4 | 0.8 | 2.4 | 2.4 |
| | 120 | 5.7 | 0.0 | 6.6 | 1.3 | 2.4 | 2.0 |
| | 240 | 2.7 | 0.0 | 5.6 | 0.3 | 1.8 | 0.9 |
| Dipel WP 12% | 30 | 8.8 | 1.2 | 10.2 | 2.9 | 3.8 | 5.0 |
| | 60 | 8.3 | 1.5 | 12.6 | 2.8 | 3.8 | 5.2 |
| | 120 | 9.3 | 2.1 | 11.2 | 4.7 | 4.5 | 4.4 |
| | 240 | 4.4 | 0.8 | 13.9 | 2.6 | 3.2 | 4.0 |
| | 490 | 5.6 | 0.3 | 10.2 | 1.9 | 2.8 | 2.7 |
| Untreated | — | 5.8 | 3.8 | 9.1 | 3.8 | 5.7 | 6.4 |

[1] Obtained 3 and 6 days after the 4th spray application; 1-2 larval instars, 3-4 larval instars
[2] On scale 0-9, obtained 5 days after the 3rd and 4th spray applications respectively. Rating represents average of 6 individually rated plants From the above data it can be seen that HD-122A applied at 60 gm/ha is more effective for controlling *Plutella xylostella*. It particularly reduces the 3-4 instar larvae which leads to reduced plant damage. As such, HD122-A is about eight times more effective than Dipel for protecting cabbage plants against attack by *Plutella xylostella*.

EXAMPLE 10

Evaluation of B.t. Strain HD-122A for the Control of Resistant *Plutella xylostella*

This test is conducted in a screen covered building with a clear plastic roof. One square meter plots each containing 9 cabbage plants (variety, Vikima) are protected with a one square meter box placed around it prior to application to eliminate the potential for contamination from adjacent plots.

Adult moths are released into the building to oviposit on the plants prior to the first treatment. The larvae are counted and recorded in two categories, 1-2 instar and 3-4 instar. Counts are made at one day pretreatment an done day before each subsequent application. Plant damage ratings are made 3 and 6 days after the treatment.

Spray applications are made to cabbage plants in sufficient amount to provide form about 17 to 240 grams per hectare of the active compound. Four applications at 4 day intervals are made and 6 plants per plot are examined for larvae counts and plant damage.

These data are reported in Table VI below. Damage ratings are determined on a scale of 0 to 9 and ratings reported are averages of 6 individually rated plants.

In this evaluation Dipel is used for comparison. This is a *Bacillus thuringiensis* var. kurstaki.

Deltamethrin is (5)-a-Cyano-3-phenoxybenzyl (1R,3R)-3-(2,2-dibromovinyl)-2,2-dimethylcyclopropanecarboxylate and is likewise used for comparison. Teflubenzuron is 1-(3,5-dichloro-2,4-difluorophenyl)-3-(2,6-difluorobenzoyl)urea and is also used for comparison in this test.

Damage Rating Systems

0 = no damage
1 = Slight or about 1 to 5% of leaf area is consumed
3 = Light or about 10 to 20% of leaf area is consumed
5 = Moderate or about 30 to 40% of leaf area is consumed
7 = Heavy or about 50 to 60% of leaf area is consumed
9 = Severe or about 70% and above of leaf area is consumed Ratings of 2, 4, 6 or 8 simply mean that the damage observed falls between the above indicated ratings and ratings shown with a decimal are average ratings from 6 plants.

The damage rating data reported in Table VI below, clearly show the superiority of the HD-122A treatments over the commercial B.t. treatments at equivalent rates. In fact, in most cases the low rate of HD-122A is superior to most of the higher rates of Dipel. The HD-122A at 120 gram ai/ha is also clearly superior to the chemical standards at both the 3 and 6 day readings.

TABLE VI

Evaluation of HD122A for Controlling resistant *Plutella xylostella* and in comparison to commercial insecticides used for control of lepidopterous insects

| Treatment | % ai | gm ai/ha | Instar # Larvae/plant[1] | | | | Damage ratings[2] | |
| --- | --- | --- | --- | --- | --- | --- | --- | --- |
| | | | 3rd day | | 6th day | | | |
| | | | 1-2 | 3-4 | 1-2 | 3-4 | 3rd day | 6th day |
| HD-122A lot A | 12% | 30 | 8.1 | 1.9 | 15.1 | 3.7 | 3.5 | 4.7 |
| | | 60 | 5.9 | 1.2 | 9.2 | 1.9 | 2.9 | 3.6 |
| | | 120 | 4.4 | 0.2 | 4.6 | 1.0 | 1.8 | 2.4 |
| HD-122A lot B | 11.8% | 30 | 9.1 | 1.9 | 15.7 | 4.5 | 4.1 | 5.4 |
| | | 60 | 7.7 | 1.8 | 11.7 | 2.4 | 3.5 | 4.7 |
| | | 120 | 5.2 | 0.9 | 7.5 | 0.7 | 2.3 | 3.3 |
| Dipel WP | 12% | 60 | 8.7 | 3.0 | 18.9 | 4.2 | 4.3 | 4.8 |
| | | 120 | 16.9 | 3.4 | 17.3 | 6.0 | 4.0 | 5.2 |
| | | 240 | 8.3 | 1.0 | 17.2 | 2.7 | 3.6 | 4.2 |
| Dipel 2X | 20% | 60 | 12.6 | 4.7 | 16.7 | 6.8 | 4.3 | 6.1 |
| | | 120 | 10.2 | 1.9 | 16.6 | 5.0 | 3.7 | 5.3 |
| | | 240 | 17.5 | 3.6 | 22.0 | 8.0 | 3.7 | 5.4 |
| Deltamethrin | 2.5% | 17 | 2.1 | 2.2 | 10.8 | 5.3 | 4.8 | 5.9 |
| | | 25 | 7.6 | 3.8 | 6.8 | 3.5 | 4.7 | 6.5 |
| Teflubenzuron | 5% | 30 | 5.3 | 2.4 | 10.2 | 3.8 | 4.9 | 5.4 |
| | | 45 | 3.2 | 1.7 | 2.7 | 2.1 | 3.1 | 4.3 |
| Untreated | — | | 10.6 | 3.6 | 16.5 | 5.4 | 5.7 | 6.9 |

[1]Obtained 3 and 6 days after the 4th spray application: 1-2 larval instars and 3-4 larval instars.
[2]On scale 0-9; obtained 3 and 6 days after the 3rd and 4th spray applications respectively. Rating represents average of 6 individually rated plants.

EXAMPLE 11

Evaluation of B.t. strain HD-122A Var. Aizawai and B.t. Strain HD263-4-5A Var. Kurstaki for the Control of Resistant *Plutella Xylostella*

This test is conducted in a screen covered building with a clear plastic roof. One square meter plots each containing 9 cabbage plants (variety, Vikima) are protected with a one square meter box placed around it prior to application to eliminate the potential for contamination from adjacent plots.

Adult moths are released into the building to oviposit on the plants prior to the first treatment. The larvae are counted and recorded in two categories, 1-2 instar and 3-4 instar. Counts are made at one day pretreatment and one day before each subsequent application. Plant damage ratings are made 3 and 6 days after the treatment.

Spray applications are made to cabbage plants in sufficient amount to provide from about 17 to 240 grams per hectare of the active compound. Four applications at 4 day intervals are made and 6 plants per plot are examined for larvae counts and plant damage.

These data are reported in Table VII below. Damage ratings are determined on a scale of 0 to 9 and ratings reported are averages of 6 individually rated plants.

In this comparison HD-263-4-5A which is derived from a kurstaki strain has a plasmid array with
    Plasmids: 130, 110+, 60+, 46+, 43, 7.5, 5.4, 5.2, 5.0, 4.9 and 1.4 Md.;

HD122-A which is derived from an aizawai strain has a plasmid array with

Plasmids: 120, 110+, 78, 50, 46+, 43, 33, 31, 6.0 (o.c.), 8.0, 5.4, 4.7, 3.5 Md and LDE.

The data from this experiment, reported in Table VII below, show a significant improvement in prevention of leaf damage using the HD122A var. aizawai strain over the HD263-4-5A var. kurstaki strain. Since HD-122A and HD263-4-5A both contain the same 46+ Md toxin plasmid, clearly the 110+ Md toxin plasmid of HD-122A and/or other characteristics of HD-122A strain background play an important part in the excellent *Plutella xylostella* control obtained with HD122A.

The damage rating system used in these tests is as follows:

Damage Rating Systems

0 = no damage
1 = Slight or about 1 to 5% of leaf area is consumed
3 = Light or about 10 to 20% of leaf area is consumed
5 = Moderate or about 30 to 40% of leaf area is consumed
7 = Heavy or about 50 to 60% of leaf area is consumed
9 = Severe or about 70% and above of leaf area is consumed Ratings of 2, 4, 6 or 8 simply mean that the damage observed falls between the above indicated ratings and ratings shown with a decimal are average ratings from 6 plants.

TABLE VII

Evaluation of B.t. strain HD-122A var. *aizawai* and B.t. strain HD263-4-5A var. *kurstaki* against *Plutella xylostella*

| B.t. Composition | gm ai/ha | Damage Rating |
|---|---|---|
| HD-122A | 30 | 2.6 |
| | 60 | 1.0 |
| HD263-4-5A | 30 | 3.5 |
| | 60 | 3.5 |

DEPOSIT OF MICROORGANISMS

It is within the scope of this invention that both sporulating and nonsporulating forms of the isolated strains of B.t. microorganisms are encompassed herein. Exemplary of the microorganisms useful in the compositions and methods disclosed herein are the following Bacillus which have been deposited with the Agricultural Research Culture Collection (NRRL), an International Depository located at 1815 N. University Street, Peoria, Ill. 61604 and which have been assigned and listed accession numbers:

| B. thuringiensis strain | Accession Numbers | Date of Deposit |
|---|---|---|
| HD-122A | NRRL-B-18406 | September 8, 1988 |
| HD-122B | NRRL-B-18407 | September 8, 1988 |
| HD-122C | NRRL-B-18408 | September and October 31, 1988 |
| HD122-1 | NRRL-B-18409 | September 8, 1988 |
| HD-263 | NRRL-HD-263 | |
| HD-263-4-5A | NRRL-B-18206 | April 27, 1987 |
| HD-279 | NRRL-HD-279 | |
| HD-279-72 | NRRL-B-18345 | |

Aspects of the present invention are not to be limited in scope by the microorganisms deposited, since the deposited embodiment is intended as a single illustration. Indeed, various modifications of the invention in addition to those shown and described herein will become apparent to those skilled in the art from the foregoing description.

What is claimed is:

1. A biologically pure culture of *Bacillus thuringiensis* var. aizawai bacterium selected from strains HD-122A deposited with NRRL and assigned accession No. B-18406; HD-122B deposited with NRRL and assigned accession No. B-18407 and HD-122C deposited with NRRL and assigned accession No. B-18408.

2. A *Bacillus thuringiensis* var. aizawai bacterium HD-122A according to claim 1, deposited with NRRL and assigned accession No. B-18406.

3. A *Bacillus thuringiensis* var. aizawai bacterium HD-122B according to claim 1, deposited with NRRL and assigned Accession No. B-18407.

4. A *Bacillus thuringiensis* var. aizawai bacterium HD-122C according to claim 1, deposited with NRRL and assigned accession No. B-18408.

5. An insecticidal composition comprising a *Bacillus thuringiensis* bacterium defined in any of claims 1 through 3, and a suitable carrier.

* * * * *